US00PP17721P3

(12) United States Plant Patent
Sanders

(10) Patent No.: US PP17,721 P3
(45) Date of Patent: May 15, 2007

(54) ***AGERATUM* PLANT NAMED 'AGBIC'**

(50) Latin Name: *Ageratum houstonianum*
Varietal Denomination: Agbic

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 92 days.

(21) Appl. No.: 11/191,201

(22) Filed: Jul. 28, 2005

(65) Prior Publication Data

US 2007/0028336 P1 Feb. 1, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Bruce Vrana

(57) ABSTRACT

A new *Ageratum* plant, characterized particularly as to novelty by its bicolor purple and violet flowers, early flowering, strongly branched plant habit and compact growth.

1 Drawing Sheet

Latin name of the genus and species of the plant claimed: *Ageratum houstonianum.*
Varietal denomination: 'Agbic'.

BACKGROUND OF THE NEW PLANT

The present invention comprises a new distinct cultivar of *Ageratum,* botanically known as *Ageratum houstonianum.* The new cultivar is propagated from cuttings resulting from the cross of 'S494-2' as female parent and 'S228A-2' as male parent. This cross was made in October 1998. 'S494-2' is not commercially available and has not been patented. 'S228A-2' is not commercially available and has not been patented.

As a result of this cross, the present cultivar was selected in August 1999 in Enkhuizen, Netherlands and has been repeatedly asexually reproduced by cuttings in Enkhuizen, Netherlands, in Gilroy, Calif., and in Sarrians, France over a three-year period. The dictinctive characteristics of this new *Ageratum* are stable and reproduced true to type in successive generations of asexual reproduction. It takes 8 to 10 weeks to produce a finished plant, depending on the temperature.

This new *Ageratum* plant is an annual in most climatical zones in the US, only in zones 9 and 10 it is a perennial plant.

SUMMARY OF THE INVENTION

The following traits have been repeatedly observed and are determined to be the unique characteristics of 'Agbic'. These characteristics in combination distinguish 'Agbic' as a new and distinct *Ageratum* cultivar:

1. Compact, upright and mounded growth habit
2. Freely branching habit
3. Freely flowering habit with many capitula in compound umbels
4. Purple and violet capitula on small green coloured leaves Plants of the new *Ageratum* differ primarily from the plants of the female parent selection in the following characteristics:

Plants of the new *Ageratum* have purple and violet coloured capitula whereas plants of the female parent selection have purple capitula. Plants of the new *Ageratum* have a compact habit with small leaves, whereas the plants of the female parent are vigorous with small leaves.

Plants of the new *Ageratum* differ primarily from the male plant selection in the following characteristics:

Plants of the new *Ageratum* have purple and violet coloured capitula whereas plants of the male parent selection have purple capitula.

DESCRIPTION OF THE DRAWING

The new *Ageratum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Ageratum.* The data which defines these characteristics were collected from asexual reproductions carried out in Enkhuizen, Netherlands. The plant history was taken on 20 weeks old plants, blossomed under natural light in the field.

Color readings were taken in the greenhouse under ambient light. Color references are primarily to The R.H.S. Colour Chart of The Royal Horticultural Society of London.

TABLE 1

Differences between the new cultivar 'Agbic' and similar cultivars

| | 'Agbic' | 'Agmontis' | 'Agsantis' |
|---|---|---|---|
| Flower color | Purple and violet | Purple | Purple violet |
| Diameter of capitulum at full flowering | 4–8 mm | 4–8 mm | 7–9 mm |

TABLE 1-continued

Differences between the new cultivar 'Agbic' and similar cultivars

| | 'Agbic' | 'Agmontis' | 'Agsantis' |
|---|---|---|---|
| Plant height | 14–18 cm | 16–20 cm | 14–18 cm |
| Diameter of plant | 28–35 cm | 30–35 cm | 28–32 cm |

The plant:

*Classification.*—Botanical: *Ageratum houstonianum.*

*Parentage.*—Female parent: Proprietary *Ageratum houstonianum* selection identified as code number 'S494-2,' not patented. Pollen parent: Proprietary *Ageratum houstonianum* selection identified as code number 'S228A-2,' not patented.

*Growth habit.*—Ascending, well branched.

*Plant height.*—14–18 cm.

*Spreading area of plant.*—28–35 cm.

*Growth rate.*—Compact.

*Strength.*—Very good.

*Branching character.*—Freely branching and lateral branching at every node.

*Blooming period.*—Year round.

The stem:

*Stem length.*—3–14 cm.

*Diameter.*—1–2.5 mm.

*Shape.*—Round.

*Color.*—RHS 145A.

*Anthocyan pigmentation.*—On stems at upper part of the plant.

*Length of internode.*—10–30 mm, depending on the light where the plant is propagated.

*Pubescence.*—Slightly pubescent.

The foliage:

*Phyllotaxis.*—Opposite, decussate and alternate.

*Shape of blade.*—Cordate.

*Texture.*—Upper side: Slightly pubescent. Lower side: Slightly pubescent.

*Venation.*—Reticulate.

*Leaf margin.*—Serrate.

*Leaf base.*—Subcordate.

*Leaf apex.*—Acute.

*Length.*—20–30 mm.

*Width.*—20–30 mm.

*Colour.*—Upper side: Dark green RHS 137A. Lower side: Medium green RHS 138A.

*Pubescence.*—Some pubescence is present.

*Length of petiole.*—4–8 mm.

*Diameter of petiole.*—0.8–2 mm.

*Color of petiole.*—RHS 138B Light green.

*Petiole surface texture.*—Slightly pubescent.

Inflorescence:

*Inflorescence.*—Compound umbel of capitula.

*Number of inflorescence per plant.*—40–60.

*Umbel size.*—3.5–5 cm.

*Umbel depth.*—1.5–3 cm.

*Length of peduncle.*—5–15 mm.

*Diameter of peduncle.*—1–2 mm.

*Color of peduncle.*—RHS N77A.

*Length of pedicel.*—5–15 mm.

*Diameter of pedicel.*—0.5–2 mm.

*Color of pedicel.*—RHS 141C.

*Number of capitula per inflorescence.*—10–20.

*Number of disc florets per capitulum.*—50–85.

*Capitulum in bud stage.*—Round, flat capitulum, showing unopened florets from the start.

*Number of ray florets.*—0.

*Shape of the corolla of the disc floret.*—Actinomorph.

*Number of lobes.*—5.

*Length of disc floret.*—3–4 mm.

*Diameter of disc floret.*—0.5–1 mm.

*Color of disc floret upper side.*—RHS 77C with tip 83A.

*Color of disc floret lower side.*—RHS 145B.

*Number of phyllaries per capitulum.*—20–30.

*Length of phyllaries.*—2–3 mm.

*Diameter of phyllaries.*—0.5–1 mm.

*Color of phyllaries.*—Upper side: RHS 137B with tip RHS 83A. Inner side: RHS 137C with tip RHS 83A.

*Diameter of capitulum at beginning of flowering.*—4–6 mm.

*Depth of capitulum.*—2–4 mm.

*Color of capitulum at beginning of flowering.*—RHS 90C.

*Diameter of capitulum at full flowering.*—4–8 mm.

*Color of capitulum at full flowering.*—RHS 90A.

Reproductive organs:

*Number of pistels.*—1.

*Shape of pistils.*—Style with two filiform branches.

*Length of stigma and style.*—4–6 mm.

*Color of stigma.*—RHS N88A.

*Inferior ovary.*—5 ribbed.

*Pappus.*—Short.

*Number of anthers.*—5, connate in a tube, filaments free.

*Shape of anthers.*—Ecalcarate.

*Pollen.*—A little pollen is present.

*Color of pollen.*—RHS 155B.

*Fragrance.*—No fragrance.

*Lastingness of the bloom.*—The capitula of one umbel open over a period of 3 to 4 weeks.

*Seedset.*—There is seedset.

Seed:

*Shape.*—Pentagonal.

*Length.*—2 mm.

*Diameter.*—0.8 mm.

*Color.*—RHS 202 A.

*Pappus.*—Very short.

Roots:

*Type of roots.*—Fibrous. Roots start to grow on every part of the stem that contacts the soil, so not only at the nodes.

Physiological and ecological characteristics: Good tolerance to heat and cold, but no frost tolerance. Strong resistance to pests and diseases.

What is claimed is:

1. A new and distinct cultivar of *Ageratum houstonianum* plant named 'Agbic,' as substantially illustrated and described herein.

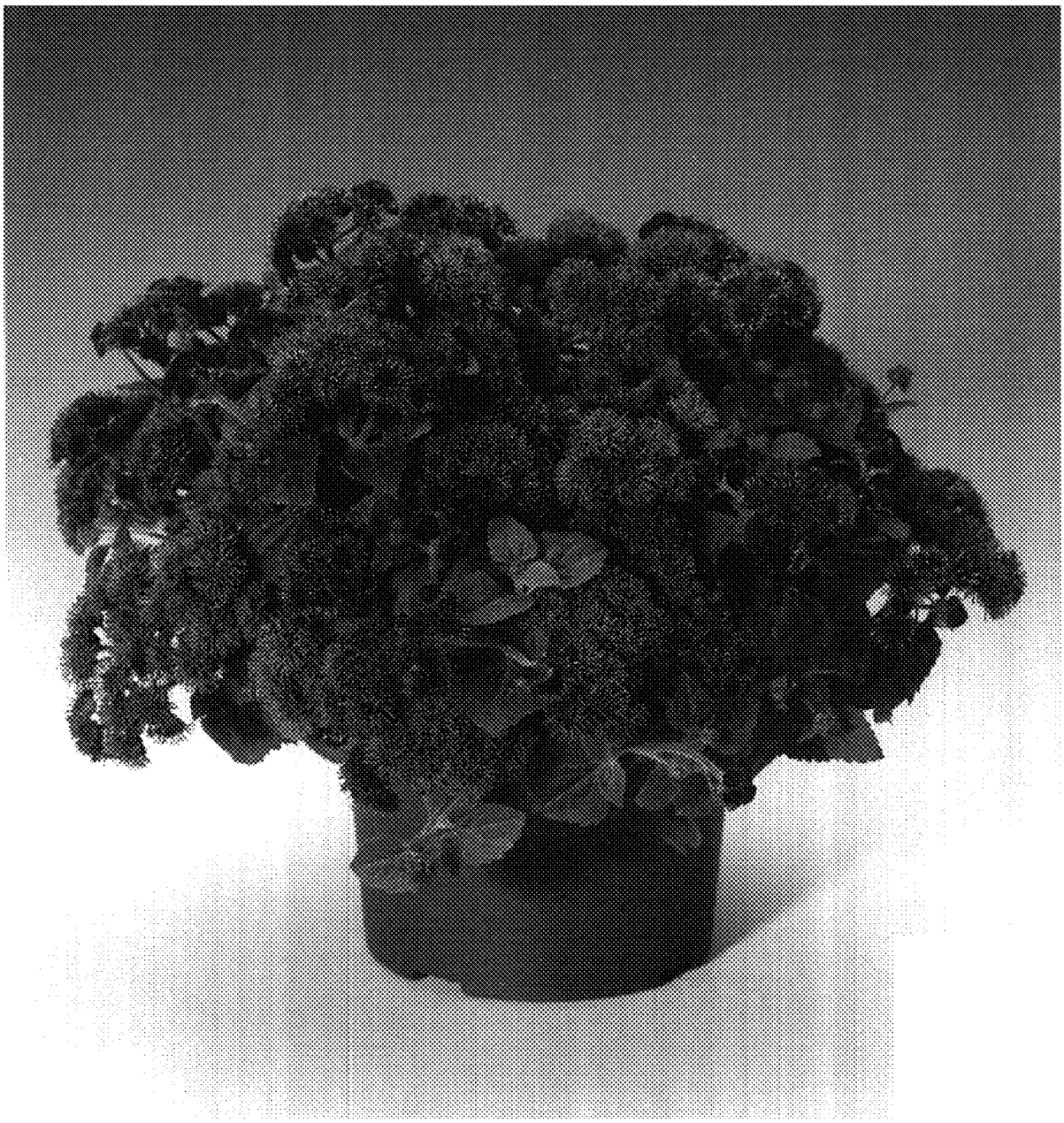

* * * * *